United States Patent
Greep et al.

(10) Patent No.: US 10,765,472 B2
(45) Date of Patent: Sep. 8, 2020

(54) ELECTROSURGICAL INSTRUMENT EXTENSION ATTACHMENT

(71) Applicant: Megadyne Medical Products, Inc., Draper, UT (US)

(72) Inventors: Darcy W. Greep, Herriman, UT (US); Paul R. Borgmeier, Salt Lake City, UT (US); Chad S. Frampton, American Fork, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 229 days.

(21) Appl. No.: 15/596,257

(22) Filed: May 16, 2017

(65) Prior Publication Data
US 2018/0333201 A1 Nov. 22, 2018

(51) Int. Cl.
*A61B 18/12* (2006.01)
*A61B 18/14* (2006.01)
*A61B 90/30* (2016.01)
*A61B 18/00* (2006.01)

(52) U.S. Cl.
CPC ...... *A61B 18/1482* (2013.01); *A61B 18/1206* (2013.01); *A61B 18/1402* (2013.01); *A61B 18/148* (2013.01); *A61B 90/30* (2016.02); *A61B 2018/0091* (2013.01); *A61B 2018/00107* (2013.01); *A61B 2018/00172* (2013.01); *A61B 2018/00404* (2013.01); *A61B 2018/00595* (2013.01); *A61B 2018/00601* (2013.01); *A61B 2018/1412* (2013.01); *A61B 2218/008* (2013.01)

(58) Field of Classification Search
None
See application file for complete search history.

(56) References Cited

U.S. PATENT DOCUMENTS

| | | |
|---|---|---|
| 4,683,884 A | 8/1987 | Hatfield |
| 5,181,916 A | 1/1993 | Reynolds |
| 5,192,267 A | 3/1993 | Shapira |
| 5,195,959 A | 3/1993 | Smith |
| 5,244,462 A | 9/1993 | Delahuerga |
| 5,318,565 A | 6/1994 | Kuriloff |
| 5,431,650 A | 7/1995 | Cosmescu |
| 5,451,223 A | 9/1995 | Ben-Simhon |
| 5,460,602 A | 10/1995 | Shapira |
| 5,662,647 A | 9/1997 | Crow |
| 5,674,219 A | 10/1997 | Monson |
| 5,693,044 A | 12/1997 | Cosmescu |
| 5,830,214 A | 11/1998 | Flom |
| 6,117,134 A | 9/2000 | Cunningham |

(Continued)

FOREIGN PATENT DOCUMENTS

WO WO 2012/155922 A2 11/2012

OTHER PUBLICATIONS

Non-Final Office Action for U.S. Appl. No. 15/596,266 dated Mar. 20, 2019.

*Primary Examiner* — Daniel W Fowler
(74) *Attorney, Agent, or Firm* — Workman Nydegger

(57) ABSTRACT

Extension attachments selectively couple to any of a variety of hand held instruments. The extension attachments may include smoke evacuation shafts and electrosurgical electrodes. The extension attachments may extend the functional capabilities of the hand held instruments, such as electrosurgical and smoke capture capabilities.

24 Claims, 5 Drawing Sheets

(56) References Cited

U.S. PATENT DOCUMENTS

| | | | |
|---|---|---|---|
| 6,146,353 A * | 11/2000 | Platt, Jr. | A61B 18/00 604/22 |
| 6,231,571 B1 | 5/2001 | Ellman | |
| 6,293,945 B1 | 9/2001 | Parins | |
| 6,355,034 B2 | 3/2002 | Cosmescu | |
| 6,379,350 B1 | 4/2002 | Sharkey | |
| 6,391,027 B1 | 5/2002 | Farin | |
| 6,530,924 B1 | 3/2003 | Ellman | |
| 6,635,034 B1 | 10/2003 | Cosmescu | |
| 6,702,812 B2 | 3/2004 | Cosmescu | |
| 6,716,211 B2 | 4/2004 | Mulier | |
| 6,802,842 B2 | 10/2004 | Ellman | |
| 7,004,939 B2 | 2/2006 | Mackay | |
| 7,083,601 B1 | 8/2006 | Cosmescu | |
| 7,112,199 B2 | 9/2006 | Cosmescu | |
| 7,198,626 B2 | 4/2007 | Lee | |
| 7,241,294 B2 | 7/2007 | Reschke | |
| 7,261,711 B2 | 8/2007 | Mulier | |
| 7,329,253 B2 | 2/2008 | Brounstein | |
| 7,387,625 B2 | 6/2008 | Hovda | |
| 7,393,351 B2 | 7/2008 | Woloszko | |
| 7,419,488 B2 | 9/2008 | Ciarrocca | |
| 7,435,247 B2 | 10/2008 | Woloszko | |
| 7,491,200 B2 | 2/2009 | Underwood | |
| 7,494,473 B2 | 2/2009 | Eggers | |
| 7,717,912 B2 | 5/2010 | Woloszko | |
| 7,824,398 B2 | 11/2010 | Woloszko | |
| 7,828,797 B2 | 11/2010 | Eggers | |
| 7,935,109 B2 | 5/2011 | Cosmescu | |
| 7,988,689 B2 | 8/2011 | Woloszko | |
| 8,002,732 B2 | 8/2011 | Visconti | |
| 8,057,470 B2 | 11/2011 | Lee | |
| 8,137,345 B2 | 3/2012 | McNall | |
| 8,187,272 B2 | 5/2012 | Sensenbrenner | |
| 8,241,278 B2 | 8/2012 | Sartor | |
| D669,581 S | 10/2012 | Van Wyk | |
| 8,317,786 B2 | 11/2012 | Dahla | |
| 8,323,279 B2 | 12/2012 | Dahla | |
| 8,460,289 B2 | 6/2013 | Sartor | |
| 8,518,018 B2 | 8/2013 | Minskoff | |
| 2001/0018586 A1 | 8/2001 | Cosmescu | |
| 2001/0051804 A1 | 12/2001 | Mulier | |
| 2002/0013582 A1 | 1/2002 | Mulier | |
| 2002/0049438 A1 | 4/2002 | Sharkey | |
| 2002/0058938 A1 | 5/2002 | Cosmescu | |
| 2002/0103485 A1 | 8/2002 | Melnyk | |
| 2003/0135208 A1 | 7/2003 | Luigi | |
| 2003/0181904 A1 * | 9/2003 | Levine | A61B 18/1402 606/45 |
| 2004/0038584 A1 | 2/2004 | Zahlit et al. | |
| 2004/0049183 A1 | 3/2004 | Ellman | |
| 2004/0162553 A1 | 8/2004 | Peng | |
| 2004/0167595 A1 * | 8/2004 | Tuominen | A61M 25/0009 607/122 |
| 2004/0172009 A1 * | 9/2004 | Marisi | A61F 5/4405 604/544 |
| 2005/0107782 A1 | 5/2005 | Reschke | |
| 2005/0113825 A1 | 5/2005 | Cosmescu | |
| 2005/0124986 A1 | 6/2005 | Brounstein | |
| 2006/0218752 A1 | 10/2006 | Potempa | |
| 2006/0264928 A1 | 11/2006 | Kornerup | |
| 2006/0276783 A1 | 12/2006 | Cosmescu | |
| 2007/0265615 A1 | 11/2007 | Ben-Simhon | |
| 2008/0103431 A1 | 5/2008 | Brounstein | |
| 2009/0062791 A1 | 3/2009 | Lee | |
| 2009/0069802 A1 | 3/2009 | Garito | |
| 2010/0094283 A1 | 4/2010 | Cosmescu | |
| 2010/0174283 A1 | 7/2010 | McNeil | |
| 2010/0234931 A1 * | 9/2010 | Jarl | A61N 1/0573 607/149 |
| 2011/0077645 A1 | 3/2011 | Lin | |
| 2011/0190768 A1 | 8/2011 | Shvetsov | |
| 2012/0101497 A1 | 4/2012 | Jayaraj | |
| 2012/0143186 A1 | 6/2012 | McNeil | |
| 2012/0203223 A1 | 8/2012 | Terry | |
| 2012/0283718 A1 | 11/2012 | Cosmescu | |
| 2012/0283728 A1 * | 11/2012 | Cosmescu | A61B 90/35 606/46 |
| 2013/0006236 A1 | 1/2013 | Creep | |
| 2013/0110108 A1 | 5/2013 | Davison | |
| 2013/0204246 A1 | 8/2013 | Creep | |
| 2014/0276763 A1 | 9/2014 | Greep et al. | |
| 2015/0126971 A1 * | 5/2015 | Muller | A61M 25/0023 604/523 |
| 2015/0180167 A1 | 6/2015 | Haas | |
| 2016/0143662 A1 | 5/2016 | Mulier | |
| 2017/0049510 A1 * | 2/2017 | Zinnanti | A61B 18/1482 |

* cited by examiner

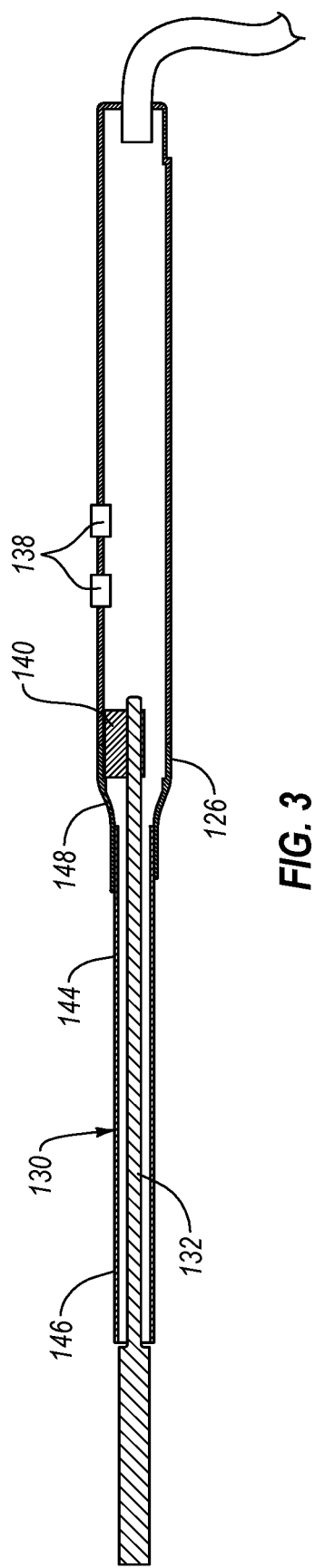
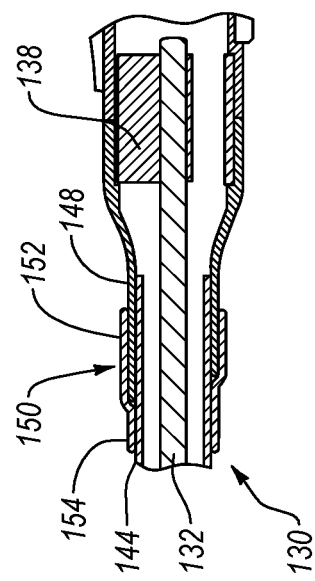
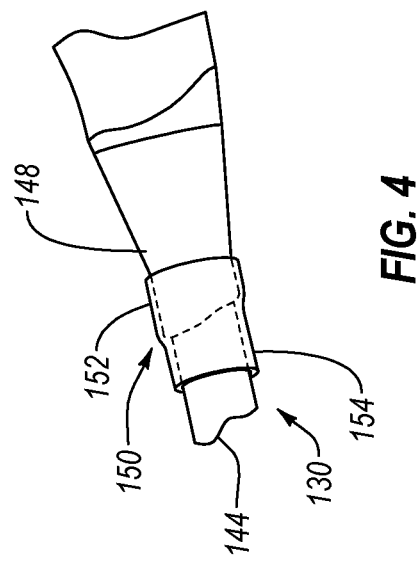
FIG. 3
FIG. 4
FIG. 5

ELECTROSURGICAL INSTRUMENT EXTENSION ATTACHMENT

BACKGROUND

1. Technical Field

This disclosure relates to electrosurgical devices. More particularly, the disclosure relates to extension attachments for electrosurgical instruments.

2. The Relevant Technology

As is known to those skilled in the art, modern surgical techniques typically employ radio frequency (RF) power to cut tissue and coagulate bleeding encountered in performing surgical procedures. For a historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. A monopolar electrosurgical generator system has an active electrode, such as in the form of an electro surgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

To make the electrical connection for the RF current between the electrosurgical generator and the electrosurgical instrument, a cable having an electrically conductive core extends from the electrosurgical generator to the electrosurgical instrument. The cable may also include a cord with additional conductors. The cord provides a connection for transmitting control signals from the electrosurgical instrument to the electrosurgical generator. The control signals may be used to cause the generator to deliver RF currents to the electrosurgical instrument for different cutting modes such as cut, coagulate, and cut-coagulate blend.

When an electrosurgical instrument is used for cutting or coagulation, smoke is commonly produced. A surgeon or assistant may use a separate smoke evacuation device to remove the smoke from the surgical field. Smoke evacuation devices commonly include a suction wand connected to a vacuum device via tubing. The surgeon or assistant holds the suction wand close to the surgical site and the smoke is drawn into the suction wand and through the tubing. However, using a smoke evacuation device separate from the electrosurgical instrument is not ideal. Using a separate smoke evacuation device requires additional hands and instruments near the surgical site, which can obscure the surgeon's view of the surgical site and reduce the room available around the surgical site for the surgeon to move.

As a result, combination electrosurgical instrument and smoke evacuation devices have been developed. These combination devices often include a hand piece that can receive an electrode or tip in a distal end thereof for performing electrosurgical procedures. The hand piece is connected to a generator via a power cable to convey RF current to the electrode or tip. Additionally, a smoke evacuation hose is connected between the hand piece and a vacuum to draw smoke away from the surgical site.

Furthermore, some existing combination electrosurgical instrument and smoke evacuation devices include an extendable portion, typically in the form of an enclosed tube, which can be selectively extended from the distal end of the hand piece. When the extendable portion is extended, the device is able to reach deeper into a surgical site to evacuate smoke. The extendable portion is typically slidably disposed within an internal chamber in the hand piece. A seal is used between the extendable portion and the internal chamber to prevent smoke from escaping the hand piece at the distal end. Similarly, a seal is used at the proximal end of the hand piece, where the smoke evacuation hose is connected to the internal chamber, to prevent smoke from escaping from the hand piece at the proximal end. Thus, the internal channel acts as part of a flow conduit through which the smoke is evacuated.

Combination electrosurgical instrument and smoke evacuation devices that utilize the foregoing extendable tube have a number of drawbacks. For instance, this arrangement usually increases the complexity of the hand piece design, assembly, and physical size. By way of example, seals must be properly disposed in both the proximal and distal ends of the hand piece in order to seal off the internal chamber and maintain the vacuum pressure therein. Additionally, the ergonomics of the hand piece are also hindered because the hand piece must remain linear to accommodate the extending portion. Further, the slidable nature of the extendable portion can make it difficult for a surgeon or operating room personnel to precisely adjust the length of the extendable portion to a particular desired length. Rather, the extendable portion often ends up being shorter or longer than the surgeon desires. Yet further, if a surgeon wants the functionality of both a standard electrosurgical instrument and a combination electrosurgical instrument with a smoke evacuation device, both instruments will need to be purchased and maintained. Understandably, purchasing and maintaining both instruments can be expensive.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 3 is a simplified cross-sectional view of the electrosurgical instrument and extension attachment of FIG. 2;

FIG. 4 is a zoomed in perspective view of the electrosurgical instrument and extension attachment of FIG. 2;

FIG. 5 is a zoomed in partial cross-sectional view of the electrosurgical instrument and extension attachment of FIG. 3;

DETAILED DESCRIPTION

The present disclosure relates to extension attachments for hand-held instruments or hand pieces that are used in the performance of various procedures and can be modified to various standard lengths while maintaining their performance capabilities. In some embodiments a hand-held instrument or hand piece is an electrosurgical instrument that holds an electrode tip in one end thereof. The electrode tip may also or alternatively be replaced with a longer electrode to facilitate performance of various procedures at greater distances. In such instances, at least a portion of the electrode tip may be enclosed by a shaft of any of various standard lengths to facilitate smoke capture. Alternatively, a hollowed electrode may be used. The hand piece may also be connected to a power cable and a smoke evacuation hose. For example, in embodiments that include an electrode tip, there may be an electrical cable that is connected to an electrosurgical generator. Also, there may be a smoke/fluid evacuation hose that is connected to a vacuum device.

Figure 1:
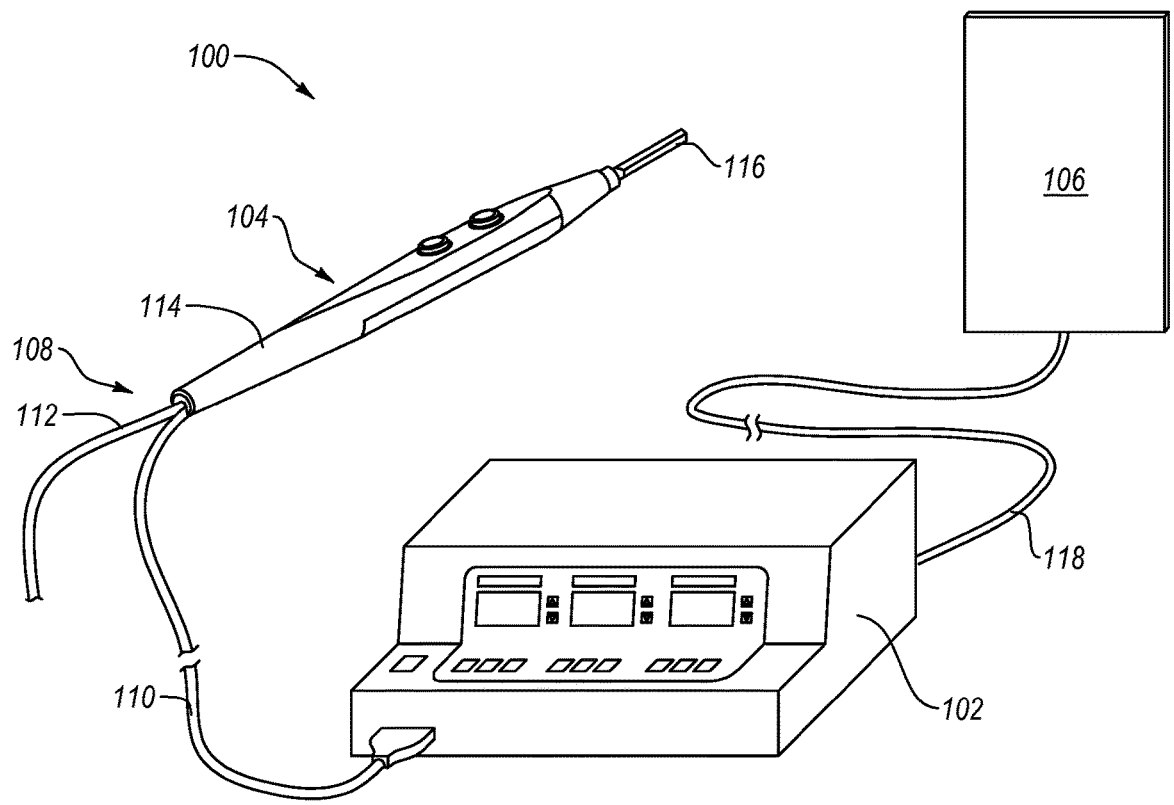
FIG. 1 illustrates an exemplary electrosurgical system.

Referring to FIG. 1, an exemplary environment is illustrated that provides one operating environment for use of the present invention. In FIG. 1, an electrosurgical system 100 is illustrated, which includes a signal generator 102, an electrosurgical instrument 104, and a return electrode 106. Signal generator 102, in one embodiment, is an RF wave generator that produces RF electrical energy. Connected to electrosurgical instrument 104 is a cable 110 that communicates the RF electrical energy from generator 102 to electrosurgical instrument 104. As also illustrated, the present embodiment also includes an evacuation hose 112 that conveys smoke and/or fluid away from a surgical site.

Generally, electrosurgical instrument 104 includes a hand piece or pencil 114 and an electrode tip 116. Electrosurgical instrument 104 communicates the RF electrical energy to a patient to cut tissue and/or cauterize blood vessels of the patient's body. Specifically, an electrical discharge is delivered from electrode tip 116 to the patient in order to cause heating of cellular matter of the patient that is in close contact with electrode tip 116. The heating takes place at an appropriately high temperature to allow electrosurgical instrument 104 to be used to perform electrosurgery. Return electrode 106 and a cable 118 provide a return electrical path to generator 102 for any excess charge that dissipates into surrounding tissue of the patient's body.

Figure 2:
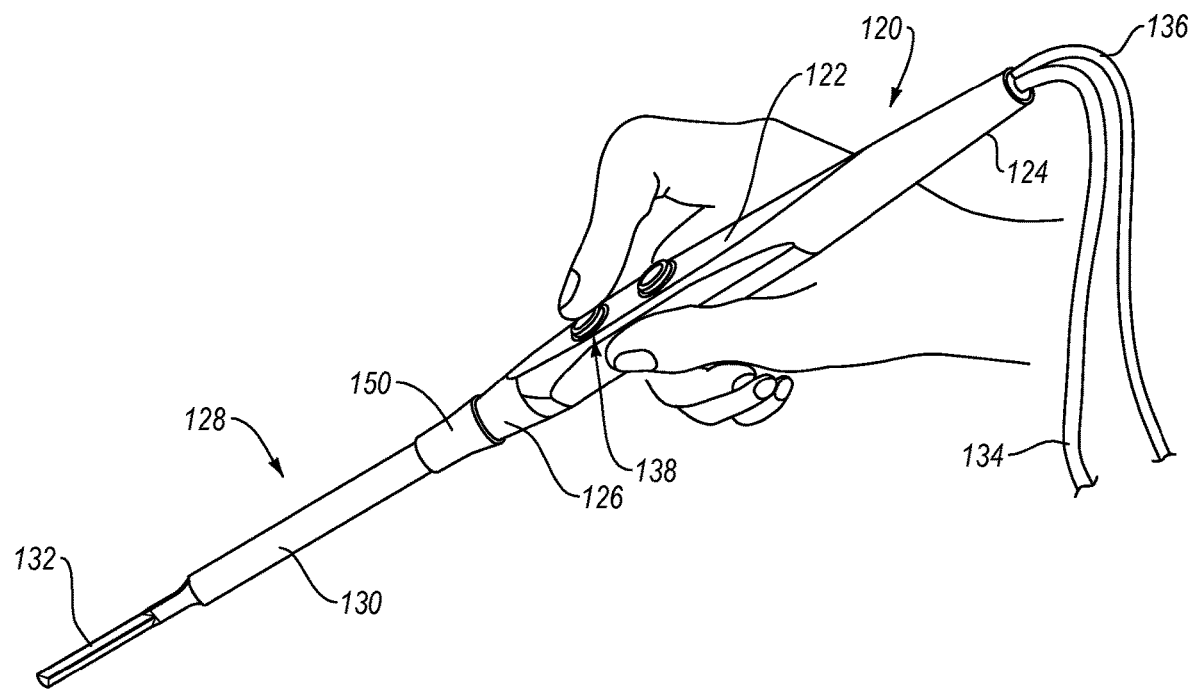
FIG. 2 illustrates an electrosurgical instrument with an extension attachment connected thereto.

Illustrated in FIG. 2 is an electrosurgical instrument 120 commonly used to perform electrosurgical procedures and evacuate smoke from a surgical site. Electrosurgical instrument 120 includes a hand piece 122 having a proximal end 124 and a distal end 126. Extension attachment 128 is selectively couplable to distal end 126 of hand piece 122. Extension attachment 128 includes a smoke evacuation shaft 130 that has a channel extending there through. Extension attachment 128 also includes an electrode tip 132 that is received through the smoke evacuation shaft 130. A power cable 134 and a smoke evacuation hose 136 are connected to electrosurgical instrument 120 at proximal end 124. Power cable 134 communicates electrical energy from an electrosurgical generator to electrosurgical instrument 120. The electrical energy is passed through electrode tip 132 and into a patient's tissue.

Smoke resulting from the electrosurgical procedure is drawn into smoke evacuation shaft 130, through an internal chamber in hand piece 122, and through smoke evacuation hose 136. A sufficient vacuum pressure must be maintained within hand piece 122 and extension attachment 128 in order to effectively evacuate smoke from the surgical site. Accordingly, the interface between the hand piece 122 and smoke evacuation shaft 130 is sealed as explained further below. Similarly, the connection between smoke evacuation hose 136 and the hand piece 122 is also sealed.

Electrosurgical instruments, such as electrosurgical instrument 120, are commonly referred to as electrosurgical pencils or pens because in use they are often held in the same or similar manner that a pencil or pen is held when writing. FIG. 2 illustrates one of the most common manners by which physicians hold electrosurgical instruments during an electrosurgical procedure. As can be seen, hand piece 122 is laid through the crook of the hand and is held in place by the middle finger and thumb. The index finger is placed on top of hand piece 122 to further hold hand piece 122 in place as well as to activate one of the input devices 138. While holding electrosurgical instrument 120 as shown in FIG. 2, a physician performs electrosurgery by activating input device 138 and moving electrode tip 132 into contact with the patient's tissue.

Attention is now directed to FIG. 3. As can be seen, disposed within distal end 126 of electrosurgical instrument 120 is a collet 140. Collet 140 can include a mount for receiving the shaft of electrode tip 132 therein. While the mount in collet 140 is shown in a centered position relative to distal end 126 of the electrosurgical instrument 120, it should be understood that the mount in collet 140 may be placed in an off-centered position, or in any other suitable position, as desired. Similarly, while FIG. 3 illustrates electrode tip 132 as being centered in smoke evacuation shaft 130, it should be understood that electrode tip 132 may be positioned in smoke evacuation shaft 130 in an off-centered manner. For instance, electrode tip 132 may be positioned closer to and/or in contact with on side of smoke evacuation shaft 130. Regardless of the positioning of collet 140 and/or electrode tip 132, collet 140 is configured to deliver electrical current to electrode tip 132 upon activation of one of the input devices 138 on hand piece 122.

Smoke evacuation shaft 130 is shown in FIG. 3 as having a uniform shape (e.g., circular) from proximal end 144 to distal end 146. However, smoke evacuation shaft 130 (as well as the other smoke evacuation shafts discussed herein) may have any number of shapes or configurations. For example, smoke evacuation shaft 130 may taper from proximal end 144 to distal end 146. Additionally, or alternatively, smoke evacuation shaft 130 may have a triangular, oval, rectangular, semi-circular, or other regular or non-regular geometric cross-sectional shape. The specific shape or other configuration of smoke evacuation shaft 130 may be selected as needed for increased visibility, pencil fit, ergonomics, connection requirements (e.g., with hand piece 120), and the like.

An outer dimension of smoke evacuation shaft 130 may remain uniform along the length of smoke evacuation shaft 130 or it may decrease from the proximal end 144 to the distal end 146. A smoke evacuation shaft 130 with an outer dimension that decreases from the proximal end 144 to the distal end 146 may provide even greater visibility as compared to a smoke evacuation shaft 130 with a uniform outer dimension. Alternatively, distal end 146 of smoke evacuation shaft 130 may be cut at a slant from one direction or multiple directions to provide better visibility of the tip. Regardless of its shape, smoke evacuation shaft 130 may have an inner dimension that provides adequate volume for effective smoke capture and air movement.

As used herein, the terms inner dimension and outer dimension are used broadly to refer to lateral dimensions or dimensions that extend transverse relative to an axis of an element. For instance, inner and/or outer dimensions may be diameters for a circular or cylindrical smoke evacuation shaft. In some embodiments, a smoke evacuation shaft may be elliptical and the inner and/or outer dimensions may be measured from one or both of the focus points to an inner or outer surface of the shaft. Similarly, a smoke evacuation shaft may be rectangular and the inner and/or outer dimensions may be measured from an axis of the shaft to an inner or outer surface of the shaft. In other embodiments, the inner and/or outer dimensions may be measured between two opposing inner or outer surfaces the shaft.

In some embodiments, unlike many common electrode tips, the substrate or shaft portion of electrode tip 132 (e.g., the portion of electrode 132 that extends through smoke evacuation shaft 130) is uninsulated. Leaving the substrate of electrode tip 132 uninsulated allows for more of the cross-sectional area of extension attachment 128 to be used as a path through which smoke can pass. Additionally, leaving the substrate of electrode tip 132 uninsulated reduces costs and manufacturing time.

In some embodiments, such as that illustrated in FIG. 3, smoke evacuation shaft 130 may have an inner dimension that is smaller than the inner dimension of nozzle 148, to which smoke evacuation shaft 130 is connected. Thus, when extension attachment 128 is connected to hand piece 120, the smoke capture may step from a macro-capture evacuation at nozzle 148 to a micro-capture evacuation at the distal end 146 of the smoke evacuation shaft 130.

As shown in FIGS. 3-5, proximal end 144 of smoke evacuation shaft 130 can be inserted into nozzle 148 of hand piece 122. Electrode tip 132 extends through the center of smoke evacuation shaft 130. Smoke evacuation shaft 130 is typically made of a material such as a polymer, plastic, resin, Silicone, Teflon, ceramic, or glass, all of which insulate smoke evacuation shaft 130 against the conduction of electrical current to nearby tissues. Accordingly, the electric current from signal generator 102 passes through electrode tip 132 without being conducted through smoke evacuation shaft 130. As such, the user can utilize electrosurgical instrument 120 and smoke evacuation shaft 130 without fearing that smoke evacuation shaft 130 will transmit electric current to unwanted, possibly sensitive areas. In other embodiments, however, smoke evacuation shaft 130 may be formed of a conductive material that is coated with an insulative material to prevent the transfer of current from smoke evacuation shaft 130 to patient tissue.

Extension attachment 128 may increase the distance between the distal end of hand piece 122 and the surgical site, thereby allowing the user to reach farther away areas with electrode tip 132 while still evacuating smoke and/or fluid from the surgical site with smoke evacuation shaft 130. It should be understood that extension attachment 128 can be of any suitable length so as to effectively increase the distance between the hand piece 122 and the surgical site.

In the illustrated embodiment, proximal end 144 of smoke evacuation shaft 130 has a circular shape and fits within nozzle 148. In some embodiments, the proximal end 144 fits snugly within nozzle 148 because the outer dimension of proximal end 144 is calibrated to fit tightly within the inner dimension of nozzle 148. In embodiments where proximal end 144 fits snugly within nozzle 148, extension attachment 128 is able to maintain its smoke capture abilities without additional sealing components.

Smoke evacuation shaft 130 may be colored and/or altered in clarity to enhance or reduce the contrast with its surroundings. Also, smoke evacuation shaft 130 may transmit light to illuminate the surgical site or other site of interest. That is, smoke evacuation shaft 130 may be made of, or include, materials or elements that transmit light, such as optical fiber or plastic.

As shown in FIGS. 3-5, a boot 150 can be placed over the overlap between nozzle 148 and proximal end 144 of smoke evacuation shaft 130 to further solidify the smoke capture abilities of the electrosurgical instrument. For example, boot 150 may have a proximal end 152 and a distal end 154. Proximal end 152 of boot 150 may fit over a portion of nozzle 148 to create a seal on nozzle 148. Similarly, distal end 154 of boot 150 may create a seal on proximal end 144 of smoke evacuation shaft 130. Thus, as illustrated in FIG. 5, even if proximal end 144 of smoke evacuation shaft 130 does not fit tightly enough within nozzle 148 to seal the connection therebetween, boot 150 may provide a sufficient seal between smoke evacuation shaft 130 and nozzle 148 to maintain the vacuum pressure therein.

While boot 150 is illustrated as fitting over the end of nozzle 148, it will be appreciated that boot 150 may be configured to seal the connection between smoke evacuation shaft 130 and nozzle 148 in various ways. For instance, the proximal end 152 of boot 150 may abut the end of nozzle 148 to seal the open space between nozzle 148 and smoke evacuation shaft 130. Additionally or alternatively, the proximal end 152 of boot 150 may extend at least partially into nozzle 148 between the interior of nozzle 148 and the exterior of smoke evacuation shaft 130. In some embodiments, an O-ring or other seal mechanism may be used in addition or as an alternative to boot 150. For instance, an O-ring may be disposed between the interior of nozzle 148 and the exterior of smoke evacuation shaft 130 to seal the connection between smoke evacuation shaft 130 and nozzle 148.

Figure 6:
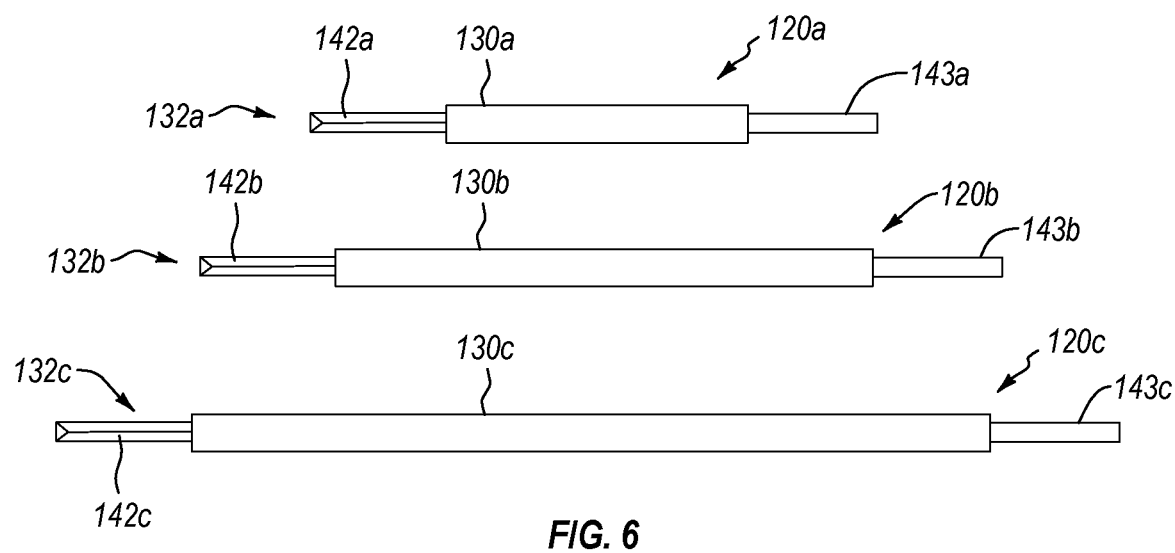
FIG. 6 is a perspective view of a set of extension attachments corresponding to one exemplary embodiment of the present invention.

Turning now to FIG. 6, there is illustrated a set of extension attachments 128 (e.g., 128a, 128b, 128c). Each of extension attachments 128 includes a smoke evacuation shaft 130 (e.g., 130a, 130b, 130c) and an electrode tip 132 (e.g., 132a, 132b, 132c). While not illustrated, each of the extension attachments 128 may also include a boot (similar to boot 150). As can be seen, each of the electrode tips 132 includes an active portion 142 (e.g., a blade, needle, hook, ball, spatula, etc.) (e.g., 142a, 142b, 142c) and a mounting portion 143 (e.g., 143a, 143b, 143c). In this illustrated embodiment, the active portions 142 and the mounting portions 143 may be connected by a shaft that extends therebetween and through smoke evacuation shafts 130. As discussed elsewhere herein, electrode tips 132 may take other forms. For instance, the active portions 142 and the mounting portions 143 may be individually formed and connected to conductive smoke evacuation shafts 130 or may be integrally formed with conductive smoke evacuation shafts 130. In any event, the active portions 142 may extend distally from distal ends of the smoke evacuation shafts 130. Likewise, the mounting portions 143 may extend proximally from proximal ends of the smoke evacuation shafts 130.

As can be seen in FIG. 6, the extension attachments 128a, 128b, 128c are of different lengths and may be used interchangeably with an instrument such as hand piece 120. For instance, depending on the surgeon's preference and/or the type of procedure being performed, the surgeon may select any one of extension attachments 128a, 128b, 128c. Furthermore, the set of extension attachments 128 allows a user to quickly and easily change the extended length during a procedure. For example, a surgeon may prefer to use extension attachment 128a during the initial stages of an operation and then may prefer to switch to extension attachment 128b or 128c during the later stages of an operation. Thus, a set of extension attachments 128 allows the user great flexibility and adaptability throughout the course of a procedure.

Figure 7:
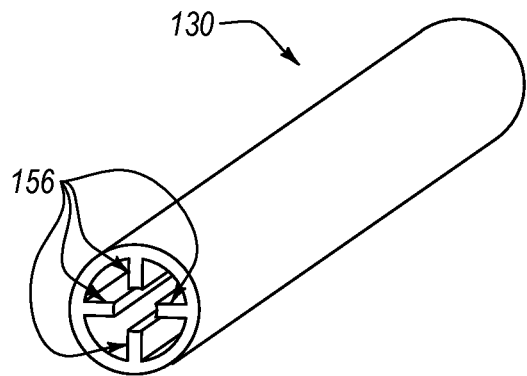
FIG. 7 is a perspective view of a shaft corresponding to one exemplary embodiment of the present invention.

Turning now to FIG. 7, the interior of one exemplary smoke evacuation shaft 130 may include structural supports, such as legs 156. In such embodiments, electrode tip 132 may run the length of smoke evacuation shaft 130 at a position in the center of the legs 156. Accordingly, legs 156 may hold electrode tip 132 within smoke evacuation shaft 130 and provide added rigidity and stability to electrode tip 132. In addition, smoke evacuation shaft 130 can still capture smoke at its distal end 146 as previously described. In particular, smoke (or other gases or fluids) may pass through smoke evacuation shaft in the areas between legs 156.

Legs 156 of smoke evacuation shaft 130 may be constructed such that they hold electrode tip 132 in such a manner so as to restrict the movement of electrode tip 132 relative to smoke evacuation shaft 130. Alternatively, legs 156 of smoke evacuation shaft 130 may be constructed to allow a user to adjust electrode tip 132 relative to smoke evacuation shaft 130.

Furthermore, while the embodiment of FIG. 7 includes four legs 156, it will be appreciated that a smoke evacuation shaft may include fewer or more legs 156. In some embodiments, the legs 156 extend the entire length of smoke evacuation shaft 130, while in other embodiments the legs 156 extend only a portion of the length of smoke evacuation shaft 130. In some embodiments, for instance, smoke evacuation shaft 130 may include a first set of legs 156 disposed along a first portion thereof and a second set of legs 156 disposed along a second portion thereof.

Figure 8:
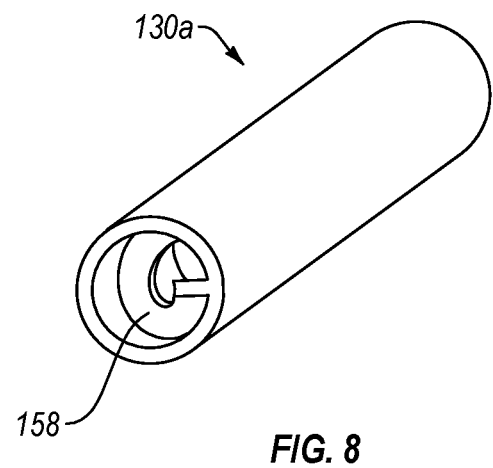
FIG. 8 is a perspective view of another shaft corresponding to an exemplary embodiment of the present invention.

The interior of smoke evacuation shaft 130 may include other configurations that allow for smoke evacuation shaft 130 to hold electrode tip 132 and capture smoke. For example, the interior of smoke evacuation shaft 130 may consist of multiple lumens of round, oval, square, triangular, rectangular, or other shapes. Further, as depicted in FIG. 8, an alternative smoke evacuation shaft 130a may include one or more internal helixes 158 that hold electrode tip 132 in place and allow for smoke to pass through smoke evacuation shaft 130a.

In some embodiments, the one or more internal helixes 158 may make at least about 1.5 rotations along at least a portion of the length of the smoke evacuation shaft 130a to effectively capture or secure the shaft of an electrode tip (e.g., electrode tip 132) therein. In some embodiments, less than 1.5 rotations of the one or more helixes 158 may result in incomplete or unstable capture of the electrode tip shaft, which could lead to rocking of the smoke evacuation shaft 130a and/or dislodgement of the smoke evacuation shaft 130a from the electrode tip shaft. In other embodiments, the one or more helixes 158 may include more than 1.5 rotations, such as for additional stability. For instance, in some embodiments, the one or more helixes 158 may make about two or more rotations along the length of the smoke evacuation shaft 130a.

In some embodiments, the one or more helixes 158 extend the entire length of smoke evacuation shaft 130a, while in other embodiments the one or more helixes 158 extend only a portion of the length of smoke evacuation shaft 130a. In some embodiments, for instance, smoke evacuation shaft 130a may include a first helix 158 disposed along a first portion thereof and a second helix 158 disposed along a second portion thereof.

In addition, it should be understood that the interior of a smoke evacuation shaft can be made with support structures of any number, shape, or size. Further, the support structures of a smoke evacuation shaft may change along the length thereof. For example, the distal end of a smoke evacuation shaft may employ a single helical extrusion as depicted in FIG. 8 while the proximal end may employ four legs as depicted in FIG. 7. Moreover, a smoke evacuation shaft as described herein may be formed in a variety of ways. For instance, a smoke evacuation shaft may be extruded, injection molded, printed, or the like. Additionally, a smoke evacuation shaft may be formed as a unitary piece, or may be assembled from multiple individually formed pieces.

Figure 9:
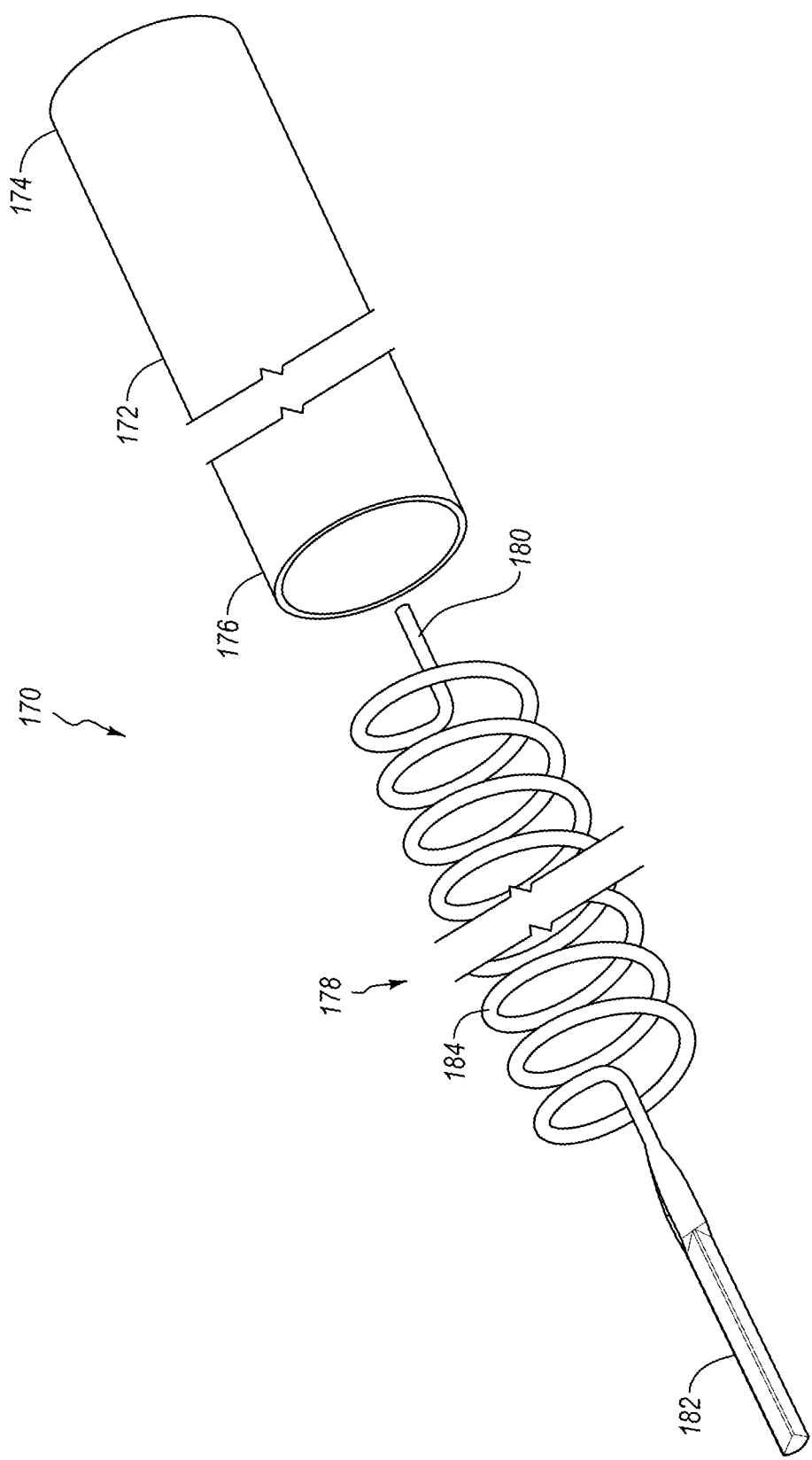
FIG. 9 is an exploded perspective view of an extension attachment corresponding to one exemplary embodiment of the present invention.

Attention is now directed to FIG. 9, which illustrates an extension attachment 170. Extension attachment 170 may be similar or identical to the other extension attachments described herein in many respects. Accordingly, particular attention will be directed to the features of extension attachment 170 that are different from the other extension attachments described herein, with the understanding that these features may replace or be combined with the other features described herein.

Extension attachment 170 includes a smoke evacuation shaft 172 that has a proximal end 174 and a distal end 176. Proximal end 174 may be inserted into a nozzle 148 on a hand piece 120 as described elsewhere herein. In the illustrated embodiment, smoke evacuation shaft 172 is hollow and defines a flow channel therethrough to allow for smoke or fluid to pass therethrough. While smoke evacuation shaft 172 is illustrated with a substantially circular cross-sectional shape, it will be appreciated that smoke evacuation shaft 172 may have other cross-sectional shapes.

In addition to smoke evacuation shaft 172, extension attachment 170 also includes an electrode tip 178. Electrode tip 178 includes an electrical contact 180, an active portion 182 (e.g., a blade, needle, hook, ball, spatula, etc.), and a shaft 184 extending between electrical contact 180 and active portion 182. Electrical contact 180 is configured to make electrical contact with an electrosurgical instrument 120. For instance, electrical contact 180 may be configured to mount within a collet 140 of electrosurgical instrument 120. Active portion 182 may be used to deliver electrosurgical current to a patient's tissue.

As with the shaft or substrate portions of the other electrode tip described herein, shaft 184 is likewise configured to convey electrosurgical current from an electrosurgical instrument to active portion 182. Unlike the straight shafts/substrates of the other electrode tips described above, however, shaft 184 is formed as a helix. The outer dimension of helical shaft 184 may generally correspond to the inner dimension of smoke evacuation shaft 172. Accordingly, electrode tip 178 may be positioned within smoke evacuation shaft 172 and helical shaft 184 may interact with the inner surface of smoke evacuation shaft 172 to hold electrode tip 178 and smoke evacuation shaft 172 together. Furthermore, even with electrode tip 178 positioned within smoke evacuation shaft 172, smoke can still pass through extension attachment 170. In particular, the smoke can pass through the flow channel in smoke evacuation shaft 172 and through helically shaped shaft 184.

While shaft 184 is illustrated in a helical form, it will be understood that shaft 184 may take other forms. For instance, shaft 184 may have a generally planar cross-sectional shape that extends between opposing interior surfaces of smoke evacuation shaft 172 so that smoke can pass on opposing sides thereof. In other embodiments, shaft 184 may have a star shaped cross-section with three, four, or more legs. The radial ends of the legs may engage the inner surface of smoke evacuation shaft 172 to hold shaft 184 within smoke evacuation shaft 172. Furthermore, smoke may pass between adjacent legs of the star shaped shaft 184 to allow the smoke to pass through extension attachment 170.

Figure 10:
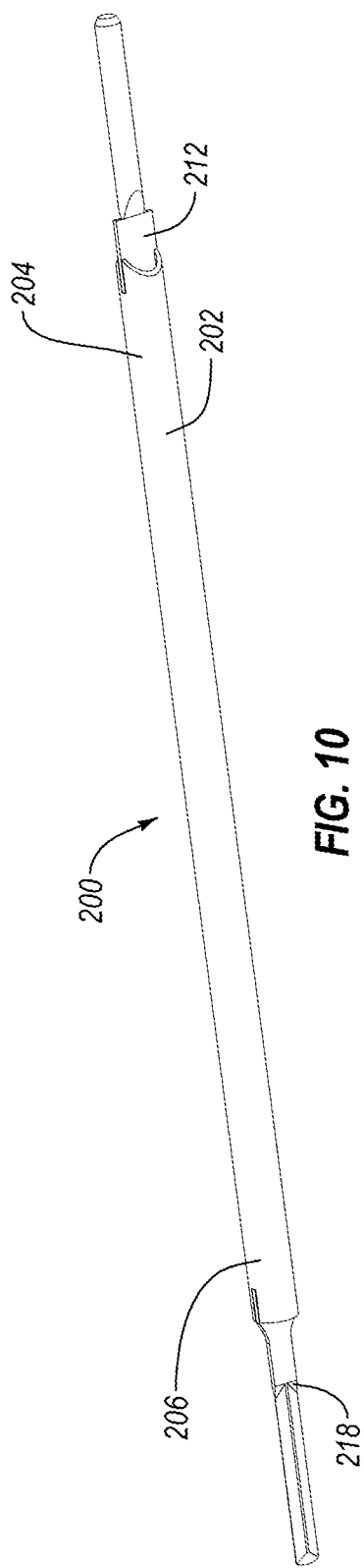
FIG. 10 is a perspective view of an extension attachment corresponding to an exemplary embodiment of the present invention.
Figure 11:
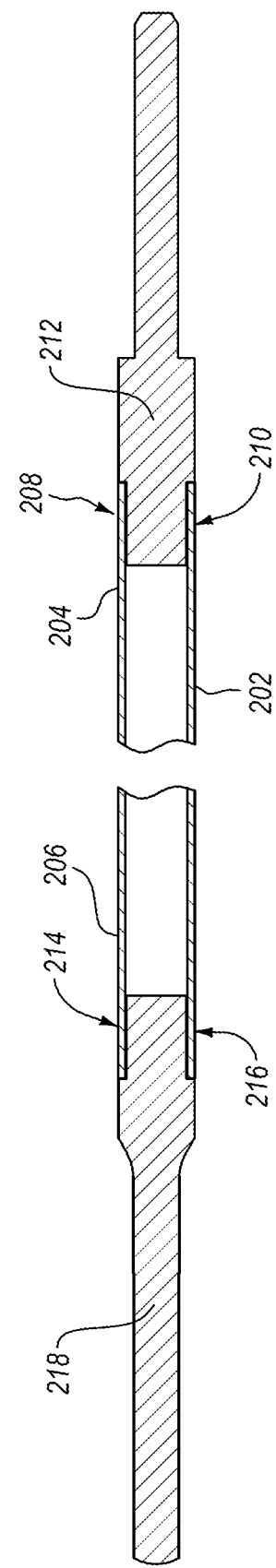
FIG. 11 is a partial cross-sectional view of the extension attachment of FIG. 10.

Attention is now directed to FIGS. 10 and 11, which illustrate an extension attachment 200. Extension attachment 200 may be similar or identical to extension attachment 128 in many respects. Accordingly, particular attention will be directed to the features of extension attachment 200 that are different from extension attachment 128, with the understanding that these features may replace or be combined with the other features described herein.

Extension attachment 200 as illustrated in FIGS. 10 and 11 includes a smoke evacuation shaft 202 that has a proximal end 204 and a distal end 206. Similar to proximal end 144 of smoke evacuation shaft 130, proximal end 204 may be inserted into a nozzle 148 on a hand piece 120. Smoke evacuation shaft 202 may be hollow or have one or more flow channels therethrough to allow for smoke or fluid to pass therethrough. While smoke evacuation shaft 202 is illustrated with a substantially circular cross-sectional shape, it will be appreciated that smoke evacuation shaft 202 may have other cross-sectional shapes.

Proximal end 204 of smoke evacuation shaft 202 includes two notches 208, 210. Notches 208, 210 on proximal end 204 of smoke evacuation shaft 202 are capable of receiving substrate 212. For example, as shown in FIG. 11, substrate 212 is cut to mate with notches 208, 210. Similarly, distal end 206 of smoke evacuation shaft 202 includes two notches 214, 216. Notches 214, 216 on proximal end 206 of smoke evacuation shaft 202 are capable of receiving blade 218. A conductive joint may be created between the notches 208, 210 and substrate 212 and between the notches 214, 216 and blade 218, such as with laser welding or other metallic bonding methods. Alternatively, a quick set adhesive or other binding material that includes conductive materials may be used to secure the connection between notches 208, 210 and substrate 212 and between notches 214, 216 and blade 218.

It should be understood that the mating relationship shown in FIGS. 10 and 11 between proximal end 204 of smoke evacuation shaft 202 and substrate 212 is illustrative only, and any suitable means of connecting substrate 212 and notches 208, 210 may be utilized. Similarly, the mating relationship between distal end 206 of smoke evacuation shaft 202 and blade 218 as shown in FIGS. 10 and 11 is illustrative only and any suitable means of connecting blade 218 and notches 214, 216 may be utilized. For example, substrate 212 and blade 218 may be connected to proximal and distal ends 204, 206, respectively, without being inserted into notches. By way of example, substrate 212 and blade 218 may be connected to proximal and distal ends 204, 206 via a press fit, compression fit, swaging, welding, or the like. Alternatively, smoke evacuation shaft 202, substrate 212, and blade 218 may be integrally formed. For instance, stamping and rolling processes may be used to form extension attachment 200 from a single piece of material.

Smoke evacuation shaft 202, substrate 212, and blade 218 may each be formed of a conductive material so as to be able to convey electrical current from a hand piece (e.g., hand piece 120) to a patient. More specifically, substrate 212 may include a mounting portion configured to connect to a collet (e.g., collet 140) and thereby receive electrical current for performing an electrical procedure. Because smoke evacuation shaft 202 is also formed of a conductive material, the electrical current received by substrate 212 may be conveyed to blade 218 by smoke evacuation shaft 202.

Thus, in contrast to other embodiments described herein, extension attachment 200 does not need an electrode tip and a separate smoke evacuation shaft to facilitate the performance of electrosurgical procedures and smoke capture. Rather, because smoke evacuation shaft 202 is formed of a conductive material, smoke evacuation shaft 202 functions both as a smoke evacuation shaft and part of the electrode that transmits electrical current to patient tissues.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An extension attachment for use with a hand piece, the extension attachment comprising:
   a hollowed smoke evacuation shaft having opposing first and second ends and a channel that extends therebetween, the first end having one or more notches formed therein and the second end having one or more notches formed therein, the one or more notches formed in the first end extending at least partially through a sidewall of the hollowed smoke evacuation shaft and from the first end towards the second end, the one or more notches formed in the second end extending at least partially through the sidewall of the hollowed smoke evacuation shaft and from the second end towards the first end, the hollowed smoke evacuation shaft being selectively couplable to an electrosurgical instrument to convey smoke from a surgical site to the hand piece through the channel;
   an electrode substrate disposed at the first end of the hollowed smoke evacuation shaft, the electrode substrate having a first portion configured for insertion in the one or more notches in the first end of the smoke evacuation shaft, the electrode substrate being configured to connect to a collet in the hand piece such that electrical current can be conveyed from the hand piece to the electrode substrate; and
   an active electrode portion disposed at the second end of the hollowed smoke evacuation shaft, the active electrode having a first portion configured for insertion in the one or more notches in the second end of the smoke evacuation shaft, the active electrode portion being configured to convey electrical current to patient tissue.

2. The smoke evacuation attachment of claim 1, wherein the hollowed smoke evacuation shaft is made of a conductive material such that the hollowed smoke evacuation shaft is configured to convey electrical current from the electrode substrate to the active electrode portion.

3. The smoke evacuation attachment of claim 1, wherein the active electrode portion comprises a blade and the electrode substrate comprises a mounting portion.

4. The extension attachment of claim 1, wherein the smoke evacuation shaft has a distal end and wherein at least a portion of the active electrode portion protrudes from the distal end of the smoke evacuation shaft.

5. The extension attachment of claim 1, wherein the smoke evacuation shaft has a proximal end and wherein at least a portion of the substrate protrudes from the proximal end of the smoke evacuation shaft.

6. The extension attachment of claim 1, further comprising a boot disposed about at least a portion of the smoke evacuation shaft, the boot being configured to seal off a connection between the smoke evacuation shaft and a hand piece when the extension attachment is coupled to the hand piece.

7. The extension attachment of claim 6, wherein the boot is configured to fit over at least a portion of a nozzle on a hand piece.

8. The extension attachment of claim 6, wherein the boot is configured to fit at least partially within a nozzle on a hand piece and between an interior surface of the nozzle and an exterior surface of the smoke evacuation shaft.

9. The extension attachment of claim 1, wherein the smoke evacuation shaft tapers from a first dimension at a proximal end to a second, smaller dimension at a distal end.

10. The extension attachment of claim 1, wherein the smoke evacuation shaft has a cross-sectional shape selected from the group consisting of: triangular, oval, rectangular, and semi-circular.

11. The extension attachment of claim 1, wherein the smoke evacuation shaft comprises at least one of: one or more light transmitting materials, one or more light transmitting elements, and one or more light emitting elements.

12. An electrosurgical instrument configured to transmit electrical energy from an electrical energy source to patient tissue and to convey smoke or fluid away from a surgical site, the electrosurgical instrument comprising:
a hand piece configured to be held by a user, the hand piece having a proximal end, a distal end, and a nozzle, wherein the nozzle comprises an opening configured to receive a portion of an electrode tip therein and through which smoke or fluid may be drawn into the hand piece;
an extension attachment that is selectively couplable to the nozzle, the extension attachment comprising:
a smoke evacuation shaft selectively couplable to the nozzle of the hand piece, the smoke evacuation shaft having a proximally directed opening at a proximal-most end of the smoke evacuation shaft, a distal end with a distally directed opening, and a channel extending between the proximal and distal ends, the smoke evacuation shaft being configured to have smoke or fluid drawn therethrough to convey the smoke or fluid to the opening in the nozzle and into the hand piece;
a helical support structure disposed within the channel and extending at least a portion of a length thereof;
an electrode tip selectively couplable to the hand piece, the electrode tip being configured to receive electrical energy from the hand piece and transmit the electrical energy to patient tissue, the electrode tip comprising an electrode substrate portion extending out of the proximally directed opening in the smoke evacuation shaft, a shaft extending through the helical support structure, and an electrode tip extending out of the distally directed opening;
a power cable for transmitting electrical energy to the hand piece; and
a smoke evacuation hose connected to the hand piece, the smoke evacuation hose being in fluid communication with the nozzle, the smoke evacuation hose being configured to convey away the smoke or fluid drawn through the smoke evacuation shaft and into the hand piece.

13. The electrosurgical instrument of claim 12, wherein the helical support structure extends radially in from an inner surface of the smoke evacuation shaft.

14. The electrosurgical instrument of claim 12, wherein the helical support structure comprises a surface that engages the electrode tip shaft to hold the electrode tip in place relative to the smoke evacuation shaft.

15. The extension attachment of claim 12, wherein the helical support structure comprises at least 1.5 rotations along the length thereof.

16. The extension attachment of claim 12, wherein the smoke evacuation shaft is made of a nonconductive material.

17. The extension attachment of claim 12, wherein the helical support structure extends the entire length of the smoke evacuation shaft.

18. The extension attachment of claim 17, wherein the helical support structure comprises a first helical support structure disposed along a first portion of the length of the smoke evacuation shaft and a second helical support structure disposed along a second portion of the length of the smoke evacuation shaft.

19. The extension attachment of claim 12, wherein the smoke evacuation shaft and the helical support structure are formed with a rigid material.

20. A fluid evacuation extension attachment for use with a hand piece, the fluid evacuation extension attachment comprising:
a fluid evacuation shaft having a proximal end, a distal end, and a channel extending therethrough between the proximal end and the distal end, the channel having an inner dimension, wherein the fluid evacuation shaft is selectively couplable to a hand piece such that fluid may be conveyed from the fluid evacuation shaft to the hand piece; and
an electrode tip mountable at least partially within the channel of the fluid evacuation device, the electrode tip comprising:
an electrical contact at a proximal end;
an active portion at a distal end thereof; and
a shaft extending between the electrical contact and the active portion, the shaft having a helical form with an outer dimension that is equal to the inner dimension of the channel, the shaft being disposed within the channel such that the shaft does not extend out of the distal end of the smoke evacuation shaft, and the outer dimension of the shaft and the inner dimension of the channel cooperating to form friction fit therebetween to secure the smoke evacuation shaft of the electrode tip to the channel of the fluid evacuation shaft in a fixed position.

21. The fluid evacuation extension attachment of claim 20, wherein the helically formed shaft is configured to be disposed within the channel of the fluid evacuation shaft.

22. The fluid evacuation extension attachment of claim 20, wherein the helically formed shaft is configured to allow smoke or fluid to flow therethrough.

23. The fluid evacuation extension attachment of claim 20, wherein the active portion of the electrosurgical electrode extends out of the distal end of the fluid evacuation shaft.

24. The fluid evacuation extension attachment of claim 20, wherein the electrical contact of the electrosurgical electrode extends out of the proximal end of the fluid evacuation shaft.

* * * * *